(12) United States Patent
Hirota et al.

(10) Patent No.: US 10,539,533 B2
(45) Date of Patent: Jan. 21, 2020

(54) WIRE ROPE FLAW DETECTION DEVICE AND ADJUSTMENT JIG

(71) Applicant: MITSUBISHI ELECTRIC CORPORATION, Chiyoda-ku, Tokyo (JP)

(72) Inventors: Kazuaki Hirota, Tokyo (JP); Takashi Yoshioka, Tokyo (JP); Yoshikazu Ota, Tokyo (JP); Hiroyuki Akita, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 7 days.

(21) Appl. No.: 15/751,659

(22) PCT Filed: Aug. 1, 2016

(86) PCT No.: PCT/JP2016/072545
§ 371 (c)(1),
(2) Date: Feb. 9, 2018

(87) PCT Pub. No.: WO2017/029977
PCT Pub. Date: Feb. 23, 2017

(65) Prior Publication Data
US 2018/0246064 A1 Aug. 30, 2018

(30) Foreign Application Priority Data
Aug. 19, 2015 (JP) .................. 2015-161741

(51) Int. Cl.
*G01N 27/72* (2006.01)
*G01N 27/87* (2006.01)

(52) U.S. Cl.
CPC .................. *G01N 27/87* (2013.01)

(58) Field of Classification Search
CPC ........ G01N 27/82; G01N 27/83; G01N 27/87; G01N 2291/2626; G01R 31/022; G01R 33/12; B66B 7/123; B66B 7/1215
See application file for complete search history.

(56) References Cited

U.S. PATENT DOCUMENTS 4,427,940 A * 1/1984 Hirama ................... B66B 7/123
324/206
5,570,017 A * 10/1996 Blum ...................... G01N 27/82
324/232

(Continued)

FOREIGN PATENT DOCUMENTS

EP 1186565 A2 3/2002
JP 55-175858 U 12/1980

(Continued)

OTHER PUBLICATIONS

International Search Report (PCT/ISA/210) dated Oct. 25, 2016, by the Japanese Patent Office as the International Searching Authority for International Application No. PCT/JP2016/072545.

(Continued)

*Primary Examiner* — Thang X Le
(74) *Attorney, Agent, or Firm* — Buchanan Ingersoll & Rooney PC

(57) ABSTRACT

The wire rope flaw detector includes: buffer members provided on both sides of the probe in an axial direction of the wire rope and between a connecting member and the probe. The connecting member is configured to connect a first and a second position regulation mechanism with each other, and is configured to guide the wire rope. The buffer members are made of a material satisfying conditions that, during running of the wire rope, a vibration frequency of the buffer members becomes lower than the vibration frequency of vibration generated by the first and the second position regulation mechanism, and have an inherent vibration frequency larger (Continued)

than the vibration frequency of the vibration having a largest amplitude among vibration components of the wire rope. The adjustment jig is used at an initial adjustment so that a guide groove of the probe is supported by the position regulation mechanisms without contact.

14 Claims, 7 Drawing Sheets

(56) References Cited

U.S. PATENT DOCUMENTS

| | | | |
|---|---|---|---|
| 2003/0075979 A1* | 4/2003 | Ueno | B62D 55/1086 305/136 |
| 2007/0090834 A1* | 4/2007 | Osada | B66B 5/125 324/240 |
| 2010/0019762 A1* | 1/2010 | Furusawa | G01N 27/83 324/240 |

FOREIGN PATENT DOCUMENTS

| | | |
|---|---|---|
| JP | 02-262048 A | 10/1990 |
| JP | 2000-337439 A | 12/2000 |
| JP | 2001-4598 A | 1/2001 |
| JP | 2005-195472 A | 7/2005 |
| JP | 2010-111456 A | 5/2010 |
| JP | 2010-256110 A | 11/2010 |
| JP | 2012-021857 A | 2/2012 |

OTHER PUBLICATIONS

Written Opinion (PCT/ISA/237) dated Oct. 25, 2016, by the Japanese Patent Office as the International Searching Authority for International Application No. PCT/JP2016/072545.

Office Action (Notification of Reason for Refusal) dated Mar. 14, 2019, by the Korean Patent Office in corresponding Korean Patent Application No. 10-2018-7001381 and English translation of the Office Action. (11 pages).

* cited by examiner

WIRE ROPE FLAW DETECTION DEVICE AND ADJUSTMENT JIG

TECHNICAL FIELD

The present invention relates to a wire rope flaw detector, which is also called a rope tester, and is configured to detect a damage of a wire rope to be used for an elevator, a hoist, a crane, and the like, and to an adjustment jig to be used at an initial adjustment of the wire rope flaw detector.

BACKGROUND ART

As a related art wire rope flaw detector, there is known a device, in which, a wire rope passing through a probe including a substantially U-shaped groove formed so as to conform a diameter of a wire rope is magnetically saturated by a magnet to detect, by a detection coil, a leakage of the magnetic flux generated from a damage portion, such as breaking of wire, to thereby detect a wire rope damaged portion (e.g., see Patent Document 1).

In Patent Document 1, the wire rope is supported by guide rollers disposed so as to across the probe on both sides in a moving direction of the wire rope so that the wire rope is prevented from contacting with the probe.

CITATION LIST

Patent Literature

[PTL 1] Japanese Patent Application Laid-open No. 2005-195472

SUMMARY OF INVENTION

Technical Problem

In the wire rope flaw detector provided with such guide roller, a gap is formed so that the wire rope and the probe are prevented from contacting with each other. The gap is secured by supporting the wire rope by the guide rollers disposed on both sides of the probe. In this case, at a contact portion of the guide roller and the wire rope, a vibration occurs, which is caused by mainly irregularities of strands of the wire rope. The vibration of this case transmits to the probe through the guide rollers, a guide roller support base, and a platform.

As a result, a gap amount between the wire rope and the probe varies due to the vibration of the probe, and hence a magnetic flux amount passing through the detection coil provided in the probe is varied compared to the wire rope. Thus, in the related art, deteriorate of flaw-detection precision due to a generated noise has been a problem.

The present invention has been made to solve the above-mentioned problem, and therefore has an object to provide a wire rope flaw detector capable of detecting the magnetic amount passing through the detection coil provided in the probe and having high flaw-detection precision without varying the gap between the wire rope and the probe.

Solution to Problem

To attain the above-mentioned problem, according to one embodiment of the present invention, there is provided a wire rope flaw detector, including: a probe including a magnetizer configured to form a main magnetic flux so as to embrace a predetermined segment in an axial direction of a wire rope, and a detection coil, which is disposed within the predetermined segment so as to be magnetically insulated from the magnetizer, and is configured to detect leakage of the magnetic flux generated from the damaged portion of the wire rope; a first position regulating mechanism and a second position regulating mechanism disposed on both sides of the probe in the axial direction of the wire rope of the magnetizer, which are configured to run the wire rope; a connecting member configured to connect between the first position regulating mechanism and the second position regulating mechanism; and a buffer member provided between the connecting member and the probe, in which the buffer member is made of a material satisfying a condition that, during running of the wire rope, a vibration frequency of the buffer member becomes lower than the vibration frequency of vibration generated by each of the first position regulation mechanism and the second position regulation mechanism.

In addition, according to the present invention, there is provided an adjustment jig, which is used for adjustment of the wire rope flaw detector, the adjustment jig including: a guide plate contact portion having a substantially U-shape, which is inserted into a substantially U-shaped portion of guide plates forming the probe; and guide roller contact portions each having a substantially U-shape, which are inserted into substantially U-shaped portions of end portions of the first position regulation mechanism and the second position regulation mechanism, and are shorter in height than the guide plate contact portions so that the wire rope is supported by the first position regulation mechanism and the second position regulation mechanism without contacting with the guide groove of the probe.

Advantageous Effects of Invention

According to the present invention, the buffer members, which are made of the material satisfying the condition that, during running of the wire rope, the vibration frequency of the buffer member becomes lower than the vibration frequency of vibration generated by each of the first position regulation mechanism and the second position regulation mechanism vibration, and are provided between the connecting member for connecting the first position regulation mechanism and the second position regulation mechanism and the probe. As a result, the vibrations generated by the contact portions between the wire rope and the position regulation mechanisms can be prevented from transmitting to the probe, and the vibration of the wire rope can be precisely detected. With this construction, there is attained such a remarkable effect that the gap between the wire rope and the probe is not varied, the magnetic flux amount passing through the detection coil is also stable, and the noise is lowered, to thereby enhance the detection precision.

DESCRIPTION OF EMBODIMENTS

First Embodiment

Figure 1:
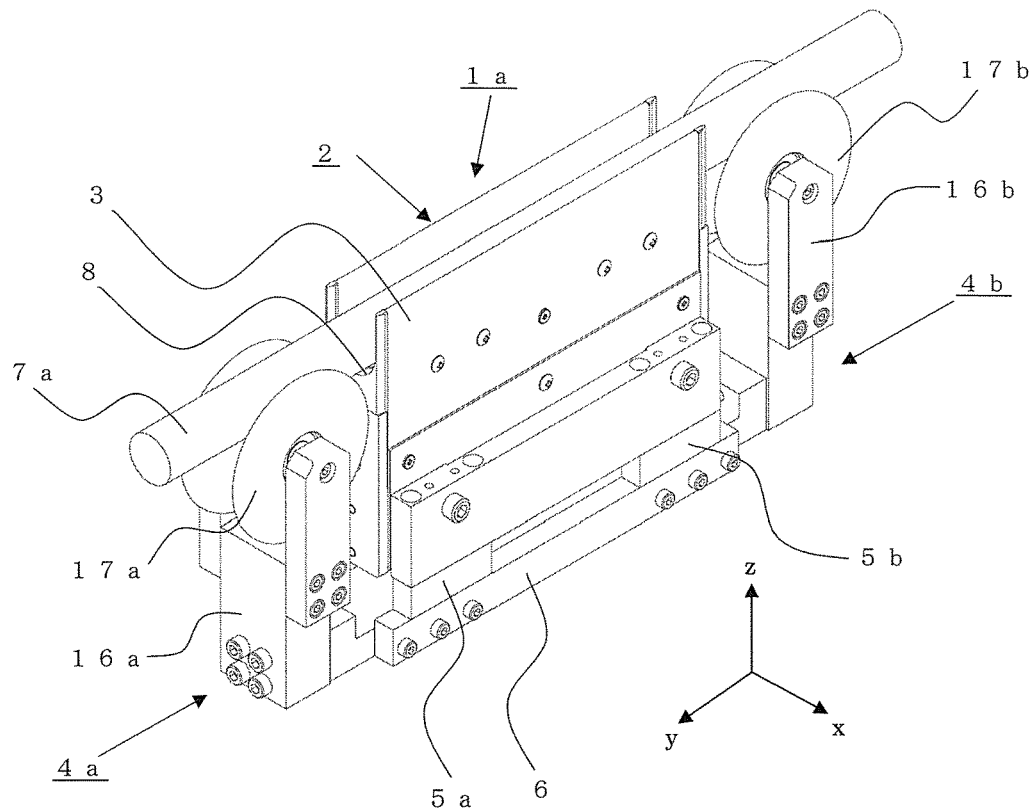
FIG. 1 is a perspective view for illustrating a wire rope flaw detector according to a first embodiment of the present invention.
Figure 2:
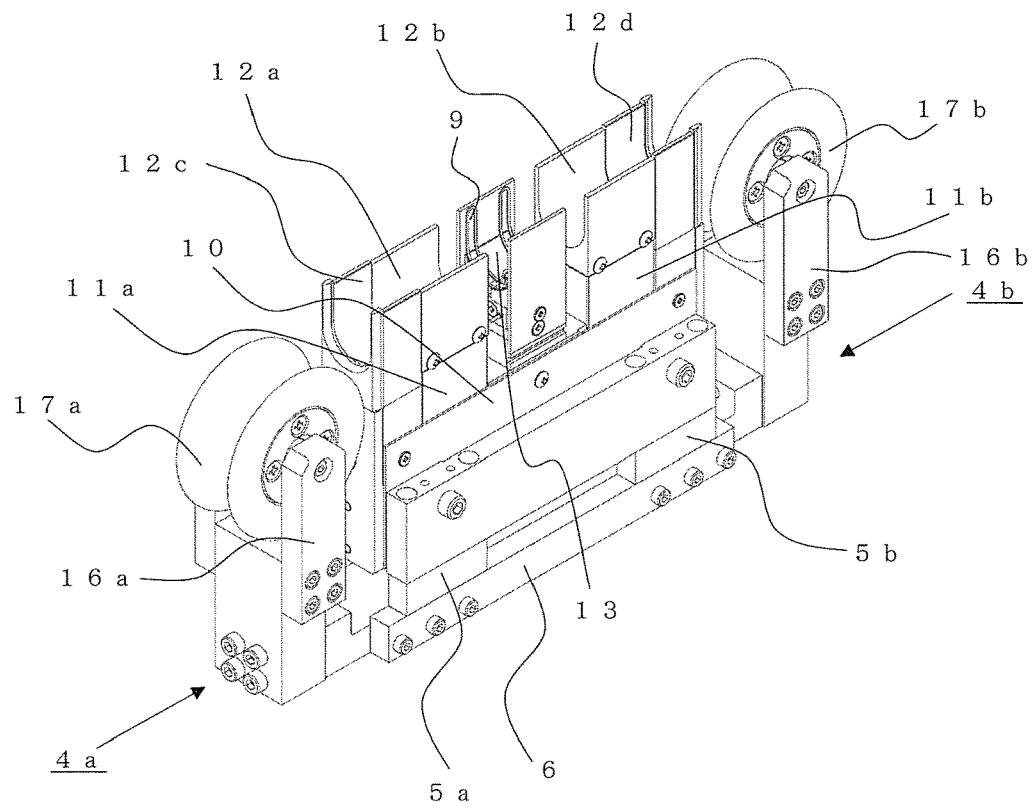
FIG. 2 is a perspective view for illustrating the wire rope flaw detector illustrated in FIG. 1 in a state in which a guide plate is removed.

FIG. 1 is a view for illustrating an appearance of a wire rope flaw detector 1a according to a first embodiment of the present invention, and FIG. 2 is a perspective view for illustrating a state in which guide plates 3, which construct a probe 2 in a wire rope flaw detector 1a illustrated in FIG. 1, are removed.

In FIG. 1 and FIG. 2, the wire rope flaw detector 1a includes: roughly divided, the probe 2 arranged at a center thereof; position regulation mechanisms 4a and 4b formed across the probe 2 at both ends thereof; buffer members 5a and 5b provided below the probe 2; and a connecting member 6 connecting between the position regulation mechanism 4a and the position regulation mechanism 4b, and being connected to the probe 2 via the buffer members 5a and 5b.

The probe 2 includes: the guide plates 3 including a guide groove 8 having a substantially U-shaped top surface on which, as illustrated in FIG. 1, a wire rope 7a is running; a detection coils 9 configured to form a main magnetic path in a predetermined segment in an axial direction of the wire rope 7a running as illustrated in FIG. 2, and to detect a leakage magnetic flux generated from a damaged portion of the wire rope 7a; magnetic pole pieces 12a and 12b each having a substantially U-shaped top surface arranged at both ends of a support base 13 having a substantially U-shaped top surface on which the detection coils 9 is bonded; the permanent magnets 11a and 11b arranged below the magnetic pole pieces 12a and 12b, respectively; U-shaped blocks 12c and 12d arranged both sides of the magnetic pole pieces 12a and 12; and a back yoke 10 arranged, in common, below the detection coils 9, the magnetic pole pieces 12a and 12b, and the U-shaped blocks 12c and 12d.

Note that, the guide plates 3 each have a substantially U-shaped unit, which are configured to, as illustrated in FIG. 1, cover the detection coils 9, the magnetic pole pieces 12a and 12b, and the U-shaped blocks 12c and 12d, and are provided with the guide groove 8. Consequently, the guide groove 8 serves as a guide grove for the probe 2, and also serves as a guide groove for the guide plates 3. The both may, hereinafter, be used in synonymous with each other.

Figure 3:
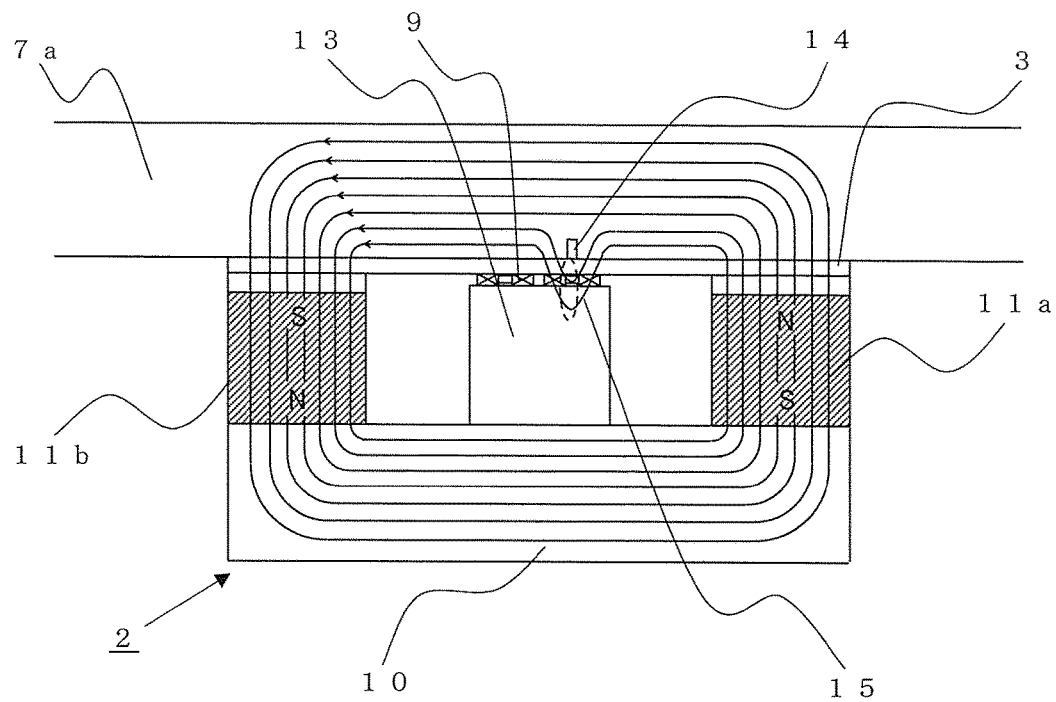
FIG. 3 is a side view for schematically illustrating a magnetizer for forming a main magnetic path within a probe in the wire rope flaw detector illustrated in FIG. 1 of the present invention.

The magnetizer in the probe 2 serves, as illustrated in FIG. 3, for forming a main magnetic flux in a predetermined segment in an axial direction of the wire rope 7a. The magnetizer of the probe 2 includes: the back yoke 10 made of a ferromagnetic material such as iron; a pair of the exciting permanent magnets 11a and 11b disposed on the upper portions of both ends of the back yoke 10 such that the polarities thereof are opposite to each other; the magnetic pole pieces 12a and 12b (not shown) formed of the ferromagnetic material disposed on a pole face on an opposite side of the permanent magnets 11 and 11b across the back yoke 10. The magnetic pole pieces 12a and 12b has a top portion having a substantially U-shape and having a curvature along an outer circumferential curvature of the wire rope 7a. The main magnetic flux of this case passes, as illustrated in FIG. 3, through the guide plates 3.

The detection coils 9 for detecting a leakage magnetic flux is bonded on the support base 13. The support base 13 is formed from a non-magnetic material so as to be magnetically insulated from a main magnetic flux path formed from the permanent magnets 11 and 11b, the magnetic pole pieces 12a and 12b, and the back yoke 10.

The guide plates 3 is made of a non-magnetic material, such as stainless, is disposed so as to be substantially closely contacted with the U-shaped portion of the magnetic pole pieces 12a and 12b while keeping a constant gap against the detection coils 9, and functions to protect the magnetic pole pieces 12a and 12b and the detection coils 9.

FIG. 3 is an illustration of a flow state of the magnetic flux when a wire rope damaged portion 14 of the wire rope 7a passes near the detection coils 9. As illustrated in FIG. 3, the main magnetic flux generated from the permanent magnet 11a passes through the guide plates 3, the wire rope 7a, and the guide plates 3, and passes the back yoke 10 via a permanent magnet 11b, and returns to the permanent magnet 11a. The local leakage magnetic flux 15 generated in the vicinity of the wire rope damaged portion 14, passes through the non-magnetized guide plates 3, the detection coils 9, and the non-magnetic support base 13, and returns to the wire rope 7a via the detection coils 9 and the guide plates 3.

Figure 4:
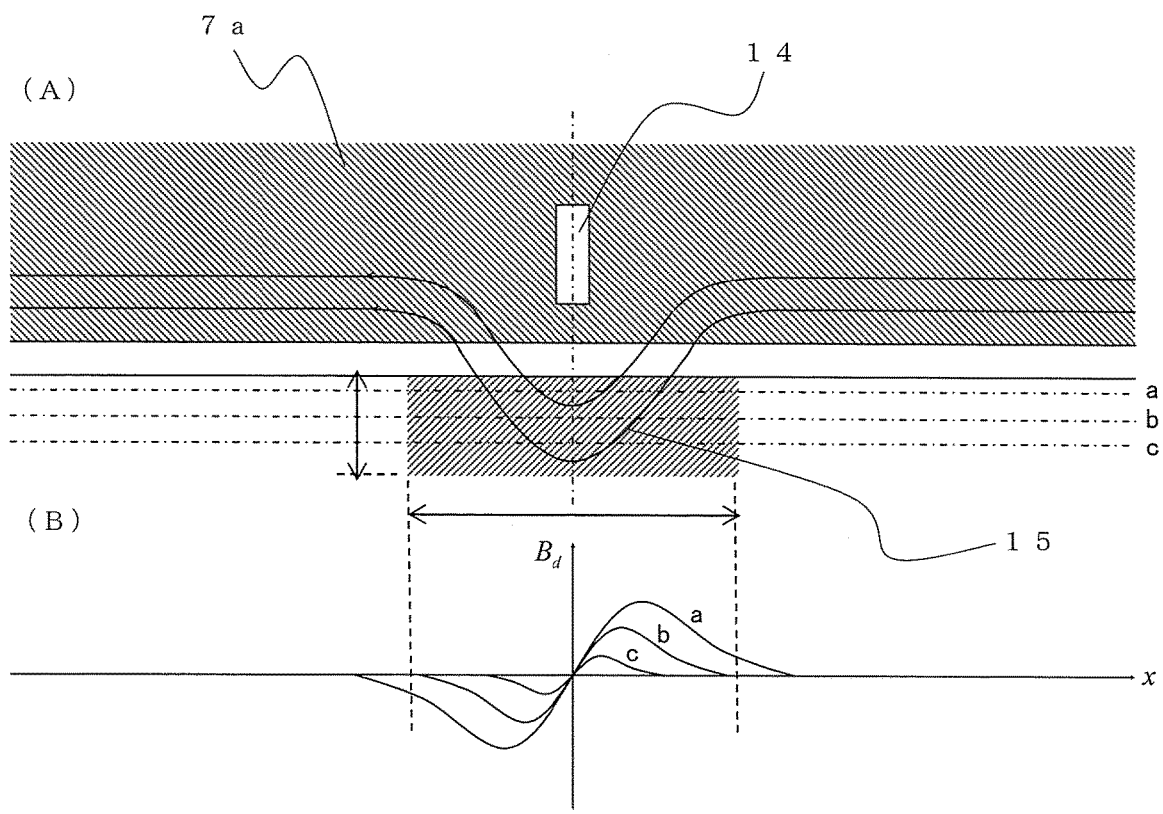
FIG. 4 is an enlarged schematic view of the main magnetic path illustrated in FIG. 3.

FIG. 4 is an enlarged view of the flow of the local leakage magnetic flux illustrated in FIG. 3. The local leakage magnetic flux 15, which flows out of the wire rope 7a, returns to the wire rope 7a through a magnetic flux path as much as shorter, and hence the area of the leakage magnetic flux to be distributed outside the wire rope 7a becomes smaller.

Here, in wave forms illustrated in FIG. 4(B), each of curves a, b, and c indicates a magnetic flux density distribution of the wire rope in a radial direction at a position of each of long dashed short dashed lines a, b, and c illustrated in FIG. 4(A). By defining the wire rope damaged portion 14 as an origin, the further away from the axial direction of the wire rope and the radial direction of the wire rope, the distribution of the magnetic flux density Bd becomes smaller. With this fact, when a distance between the wire rope 7a and the detection coils 9 varies, the magnetic flux density Bd varies, with the result that a change in detection signal intensity can be found. Consequently, based on the change in detection signal intensity, through determination of a change in distance between the wire rope 7a and the detection coils 9, wire rope damaged portion 14 can be detected.

Figure 5:
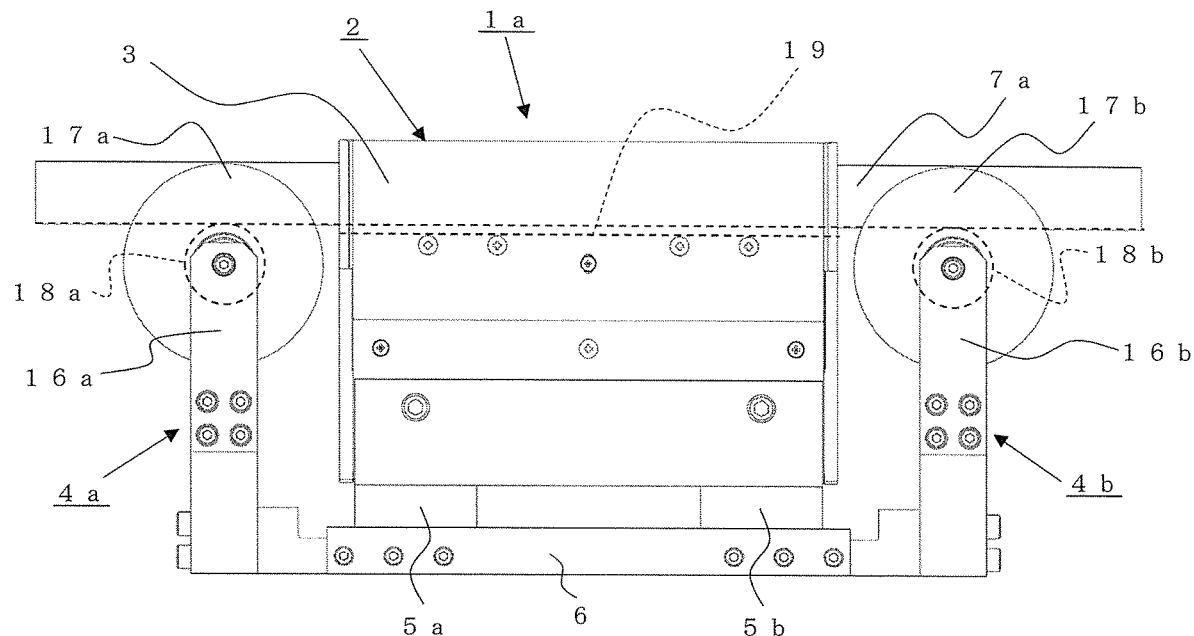
FIG. 5 is a side view for illustrating the wire rope flaw detector according to the first embodiment of the present invention.
Figure 6:
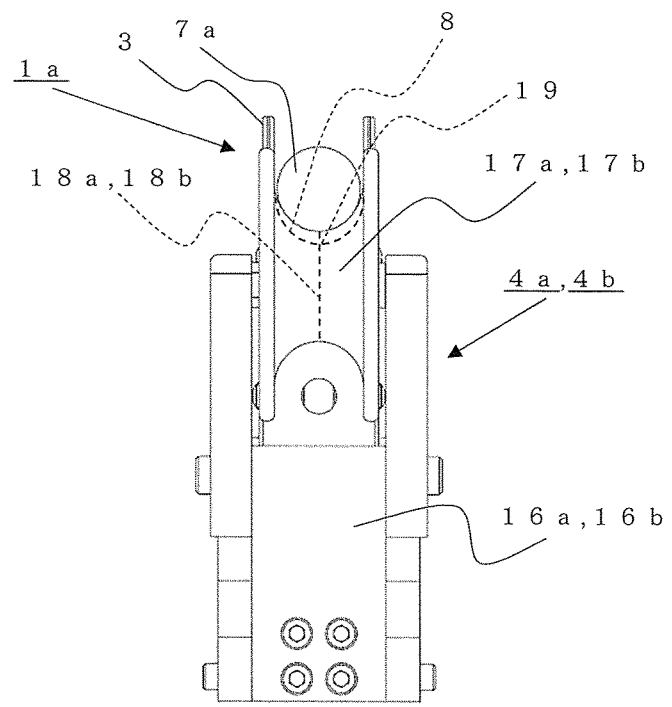
FIG. 6 is a front elevational view for illustrating the wire rope flaw detector according the first embodiment of the present invention.

FIG. 5 is an illustration of the wire rope flaw detector 1a, when viewed from its side, according to a first embodiment 1 of the present invention illustrated in FIG. 1, and FIG. 6 is an illustration of the wire rope flaw detector 1a when viewed from its front.

Now, description is made of the position regulation mechanisms 4a and 4b using FIG. 5 and FIG. 6. The position regulation mechanisms 4a and 4b include the guide roller support members 16a and 16b, respectively, and the guide rollers 17a and 17b configured to guide the wire rope 7a, which are supported in a rotatable manner by the guide roller support members 16a and 16b, respectively.

The position regulation mechanisms 4a and 4b are configured to bring the rotatable guide rollers 17a and 17b into contact with the wire rope 7a. The position regulation mechanisms 4a and 4b are also configured to bring the probe 2 into non-contact state, with a given gap, between the guide plates 3 and the wire rope 7a. With this structure, the position regulation mechanisms 4a and 4b have a function of suppressing the vibration, which is generated when the wire rope 7a is in a slide running state on the guide plates 3, and also have a function of preventing the guide plates 3 from wearing.

The guide rollers 17a and 17b each having an outer circumferential surface bent into a U-shape include, at the center portion of the outer circumferential surfaces, minimum diameter portions 18a and 18b having a round shape and being the shortest from the rotation centers thereof. Further, the guide rollers 17a and 17b each include, on both sides of the minimum diameter portions 18a and 18b (both right and left sides in FIG. 6), a pair of sloped portions whose diameter from the rotation center becomes larger as approaching toward opposite directions from the minimum diameter portions 18a and 18b. Then, the rotation axis is provided so as to be orthogonal to the direction of the guide groove 8 of the guide plates 3 of the probe 2, and a depth direction of the guide groove 8 of the guide plates 3 of the probe 2, The highest top portions of the minimum diameter portions 18a and 18b of the outer circumferential portions, as illustrated in FIG. 6, are disposed a little upper than the lowest portion 19 of the guide groove 8 of the guide plates 3.

Specifically, in the minimum diameter portions 18a and 18b, each having the round shape, of the outer circumferential surface of the guide rollers 17a and 17b constructing the position regulation mechanisms 4a and 4b arranged on both sides of the probe 2, a tangent line on a side of being contact with the wire rope 7a has a constant gap between the guide plates 3. That is to say, without penetrating the guide plates 3, the guide rollers 17a and 17b of the position regulation mechanisms 4a and 4b are arranged so as to be substantially parallel, with a slight gap, to a straight line forming a lowest portion 19 of the guide groove 8 of the guide plates 3.

Next, with reference to FIG. 1, the buffer members 5a and 5b are described.

The buffer members 5a and 5b are arranged between the probe 2 and the connecting member 6, and hence the probe 2 and the connecting member 6 are not directly connected with each other. The materials of the buffer members 5a and 5b are mainly made of a thermosetting resin, such as polyurethane and silicon, or a thermoplastic resin, such as a phenol resin, polyethylene, a phenol resin, polypropylene, polystyrene, polyvinyl chloride, ABS, and PET, each having a smaller Young's modulus compared to a steel material or an aluminum material used for the probe 2, the position regulation mechanisms 4a and 4b, and the connecting member 6. With this construction, the buffer members 5a and 5b have an effect of suppressing the vibration generated at the contact portion between the wire rope 7a and the position regulation mechanisms 4a and 4b from transmitting to the probe 2. That is, the probe 2 is in a non-contact state with the wire rope 7a by virtue of the position regulation mechanisms 4a and 4b, and hence the frequency of vibration to be generated by the probe 2 is equal to the frequency of the vibration of each of the buffer members.

The material of the buffer members 5a and 5b is a material having a small Young's modulus as described above. However, the Young's modulus has limiting factors such as an upper limit and a lower limit. For example, regarding the upper limit, in a case in which Young's modulus of the buffer members 5a and 5b is extremely high, that is, when a stiff material is used, the vibration generated by the contact portion between the wire rope 7a and the position regulation mechanisms 4a and 4b is liable to be directly transmitted to the probe 2.

Further, regarding the lower limit, too, the wire rope 7a itself vibrates during the running. However, in a case in which the Young's modulus of the buffer members 5a and 5b is extremely low, that is, when a soft material is used, the probe 2 may not follow the vibration of the wire rope 7a, and hence the distance between the wire rope 7a and the detection coils 9 varies, resulting in generating a noise as a risk. In other word, the buffer members 5a and 5b are required not to follow the vibration to be generated at the contact portion between the wire rope 7a and each of the position regulation mechanisms 4a and 4b, and are required, meanwhile, to follow the vibration of the wire rope 7a. In such a meaning, it is desired that the buffer members 5a and 5b be made of a material having Young's modulus satisfying that conditions.

Here, regarding the selection of the material of the buffer members 5a and 5b, and its characteristics calculation method is specifically described.

Generally speaking, right or wrong of the follow is determined by an inherent frequency of vibration. Against a specific vibration, the material having an inherent frequency than the frequency of the specific vibration follow the vibration. However, the material having a lower inherent frequency of vibration than the frequency of the specific vibration does not follow the vibration. Thus, assuming that: the inherent frequency of vibration of the buffer members 5a and 5b in a z direction is represented as Fk; a main vibration frequency (vibration frequency of vibration having a largest amplitude among vibration components of the wire rope) of the wire rope 7a is represented Fw; and the vibration frequency of vibration generated at the contact portion between the wire rope 7a and the position regulation mechanisms 4a and 4b is represented by Fi, the following expression must be established.

$$Fw<Fk<Fi \qquad \text{Expression (1)}$$

It should be noted that, in a case in which Fw=Fk is established, or in a case in which a difference between Fw and Fk is not large, compared to a related art, a noise reduction effect can be acquired. To achieve the effect with more reliability, it is desired that Fw<Fk<Fi be established like the above-mentioned Expression (1).

Note that, the main vibration frequency Fw is a value available by a displacement sensor by an on-site actual measurement of the vibration of the wire rope. Further, the main reason of the vibration, which is generated at the contact portion between the wire rope 7a and each of the position regulation mechanisms 4a and 4b, is due to irregularities of the strands on a surface of the wire rope 7a. Thus, assuming that a gap of the strands forming the wire rope 7a in a running direction of the wire rope is represented as P, and a running speed of the wire rope at a measurement time by the wire rope flaw detector is represented as V, the vibration frequency Fi is calculated by Fi=V/P.

Assuming that, in a plane parallel to xy surface, a cross-sectional area, which is obtained by cutting the buffer members 5a and 5b, is represented as A, a dimension in a Z direction is represented as t, Young's modulus is represent as E, and a spring constant is represented as k, K=A*E/t is established according to Hooke's law. Consequently, assuming that a mass of the probe 2 is represented as in, the value Fk can be calculated by Fk=√/(A*E/t/m)/(2*π).

Consequently, the materials of the buffer members 5a and 5b may be selected, by substituting the inherent vibration frequency Fk and the vibration frequency Fi into the above-mentioned Expression (1), among materials having Young's modulus satisfying the following Expression (2).

$$Fw < \sqrt{(A*E/t/m)/(2*m)/(2*\pi)} < /P \quad \text{Expression (2)}$$

It should be noted that a running speed V of the wire rope is a value that varies depending upon a construction or a setting of a drive system for driving the wire rope, and hence it is desired to use, as the running speed V of the wire rope, a minimum value among the running speeds that may be assumed.

However, in a case in which the lowest value of the running speed V of the wire rope is a minimum value, there is a risk in that the buffer members satisfying the above-mentioned Expression (2) may not be designed. In such a case, the buffer members may be designed so that the value A*E/t becomes lowest within a range in which a designing of the buffer members is available. Except for a case in which the running speed V of the wire rope is minimum, there may be obtained a vibration transmittance suppression effect by virtue of the buffer members.

Further, in this embodiment, regarding a number of the buffer members, description is made of a case in which two pieces are used, but is not limited to two pieces. One piece or three pieces of the buffer members may be used as long as satisfying the above-mentioned Expression (2). For example, when employing such a configuration that four pieces of the buffer members are used to be arranged at respective four corners of the probe, a posture of the probe may be made more stable.

Meanwhile, the buffer members 5a and 5b are made of a resin material, and hence dimensional precision may not be easily obtained. Accordingly, there is a risk in that the positional relationships between the guide groove 8 of the guide plates 3 and concave portions of the guide rollers 17a and 17b may cause. In a case in which the positional relationships between the guide groove 8 of the guide plates 3 and the concave portions of the guide rollers 17a and 17b are displaced, the wire rope 7a is brought into contact with the guide groove 8 of the guide plates 3, vibration may be generated to enlarge a noise. To prevent this symptom, after fabricating all parts of the wire rope flaw detector 1a and before performing a flaw measurement, an adjustment operation is required for adjusting the positional relationships between the guide groove 8 of the guide plates 3 and the concave portions of the guide rollers 17a and 17b.

<Adjustment Jig>

Figure 7:
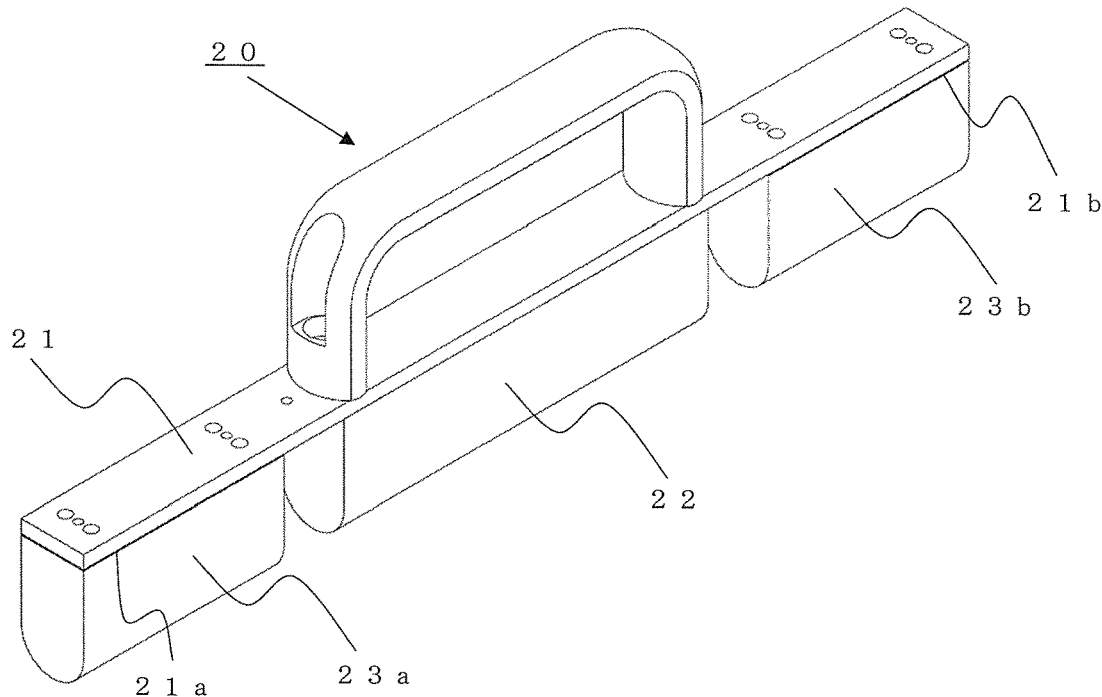
FIG. 7 is a perspective view for illustrating an adjustment jig, which is used when an adjustment operation is carried out for the wire rope flaw detector of the present invention.
Figure 8:
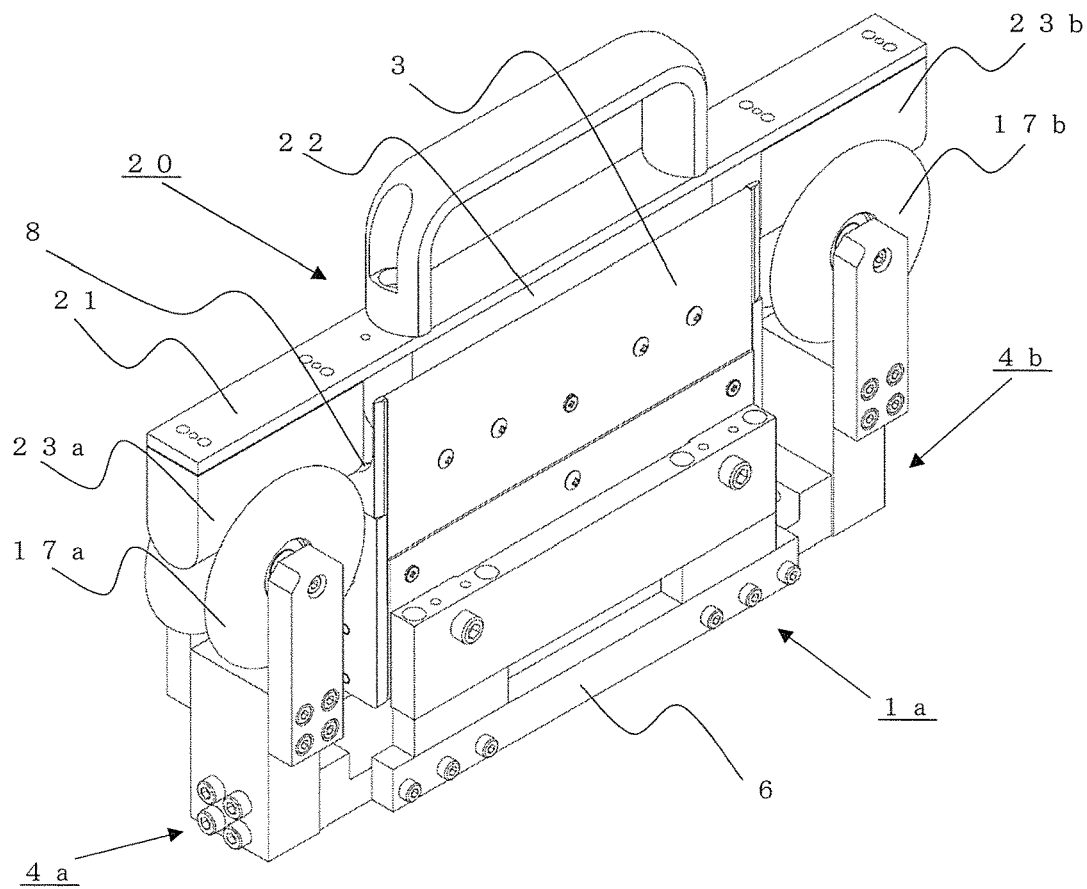
FIG. 8 is a perspective view for illustrating a state of the adjustment operation carried out by the adjustment jig illustrated in FIG. 7.

FIG. 7 is an illustration of an adjustment jig 20 for adjusting the positional relationships between the guide groove 8 of the guide plates 3 and the concave portions of the guide rollers 17a and 17b, and FIG. 8 is an illustration for illustrating a state of the operation for adjusting the positional relationships between the guide groove 8 of the guide plates 3 and the concave portions of the guide rollers 17a and 17b. This adjustment operation is carried out using a dedicated adjustment jig 20. In the adjustment jig 20, a guide plate contact portion 22 is disposed at a center of a base plate 21, and the guide roller contact portions 23a and 23b are disposed at both ends of the guide plates. The guide plate contact portion 22 is formed of a ferromagnetic material such as iron.

The each of ends of the guide plate contact portion 22 and the guide roller contact portions 23a and 23b has a semi-circular shapes, and its radius is set as equivalent to the radius of the wire rope 7a. Further, a height of the end of the guide plate contact portion 22 is a little higher than the ends of the guide roller contact portions 23a and 23b. Under this state, the spacers 21a and 21b are inserted between the guide roller contact portions 23a and 23b and a base plate 21, and hence it is configured such that vertical relationships between the height of the end of the guide plate contact portion 22 and the heights of the ends of the guide roller contact portions 23a and 23b may freely be adjustable.

In the adjustment operation, the position regulation mechanisms 4a and 4b are removed in advance from the connecting member 6. Otherwise, for example, when engagements between the connecting member 6 and the position regulation mechanisms 4a and 4b are made with screws, the screws are loosened to allow the position regulation mechanisms 4a and 4b to be movable states. Under this state, the guide roller contact portions 23a and 23b of the adjustment jig 20 are attracted to the guide groove 8 of the guide plates 3 of the wire rope flaw detector 1a using magnetic forces of the permanent magnets 11 and 11b of the probe 2. At the same time, while the concave portions of the guide rollers 17a and 17b of the position regulation mechanisms 4a and 4b are pressed against the guide roller contact portions 23a and 23b of the adjustment jig 20, the position regulation mechanisms 4a and 4b and the connecting member 6 are connected with each other, or the position regulation mechanisms 4a and 4b are immobilized.

According to this method, the positional relationships between the guide groove 8 of the guide plates 3 and the concave portions of the guide rollers 17a and 17b of the position regulation mechanisms 4a and 4b may be aligned with the positional relationships of the guide plate contact portion 22 and the guide roller contact portions 23a and 23b of the adjustment jig 20, and hence the positional relationships between the guide groove 8 of the guide plates 3 and the concave portions of the guide rollers 17a and 17b of the position regulation mechanisms 4a and 4b are determined with high accuracy.

Further, by adjusting the height relationships between the guide plate contact portion 22 and the guide roller contact portions 23a and 23b, the height relationships between the guide groove 8 of the guide plates 3 and the concave portions of the guide rollers 17a and 17b may be adjusted, and hence the gap amount between the wire rope 7a and the guide groove 8 of the guide plates 3 may be become adjustable.

According to the construction, the guide rollers 17a and 17b of the position regulation mechanisms 4a and 4b are brought into contact with the wire rope 7a, and also a gap is generated between the guide plates 3 of the probe 2 and the wire rope 7a. As a result, the vibration, which is generated when the wire rope 7a runs slidingly on the guide plates 3, may be prevented from generating. At the same time, the buffer members 5a and 5b are arranged between the position regulation mechanisms 4a and 4b and the connecting member 6 and the probe 2, and hence the vibration generated at the contact portions between the guide rollers 17a and 17b of the position regulation mechanisms 4a and 4b and the wire rope 7a may be prevented from transmitting to the probe 2.

With those vibration prevention effects, the vibration frequency of vibration generated between the buffer members 5a and 5b and the probe becomes lower than the vibration frequency of vibration generated at the contact portions between the guide rollers 17a and 17b of the position regulation mechanisms 4a and 4b and the wire rope 7a. Accordingly, the gentle change in gap between the wire rope 7a and the detection coils 9 may be achieved, and hence a signal to be generated when the wire rope flaw detector 1a has found a flaw portion 14 of the wire rope 7a and a frequency band of a noise to be generated due to the change in gap may be changed. Consequently, by cutting the frequency band only of the noise with an analog circuit or by digital filter processing, the detection precision of the flaw portion 14 of the wire rope 7a may be enhanced.

Second Embodiment

Figure 9:
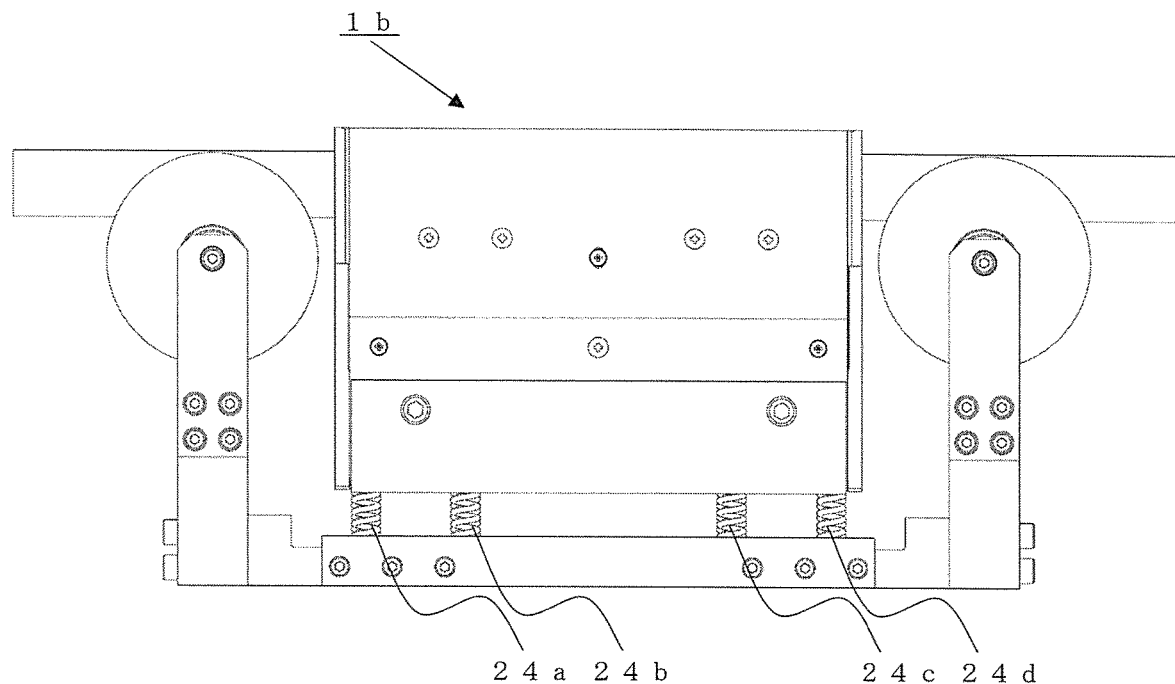
FIG. 9 is a side view of a wire rope flaw detector according to a second embodiment of the present invention.

FIG. 9 is an illustration of a wire rope flaw detector 1b according to a second embodiment of the present invention. In the above-mentioned first embodiment, as the material of the buffer members 5a and 5b, the thermosetting resin or the thermoplastic resin is mentioned. However, instead of them, as illustrated in FIG. 9, springs 24a, 24b, 24c, and 24d may be used. In such a case, as well as the thermosetting resin or the thermoplastic resin, the spring is also imposed on the following condition. Assuming that a spring constant of the springs 24a, 2b, 24c, and 24d is represented as k, it is required to satisfy $Fw < \sqrt{(k/m)}/(2*\pi) < V/P$ (each value is the same with one in the first embodiment).

The springs 24a, 2b, 24c, and 24d, compared to the above-mentioned thermosetting resin or the thermoplastic resin, may easily be changed in its spring constant k by changing a cross-sectional area or the number of winding thereof. Further, in the case of spring, there are many options in its material such as a piano wire, a steal wire, or stainless, and hence even in a case in which there is no material suited for the thermosetting resin of the thermoplastic resin, because the range satisfying the above-mentioned conditional Expression (2) is too narrow, the buffer members satisfying the above-mentioned conditional Expression (2) may be formed.

Third to Fifth Embodiments

Figure 10:
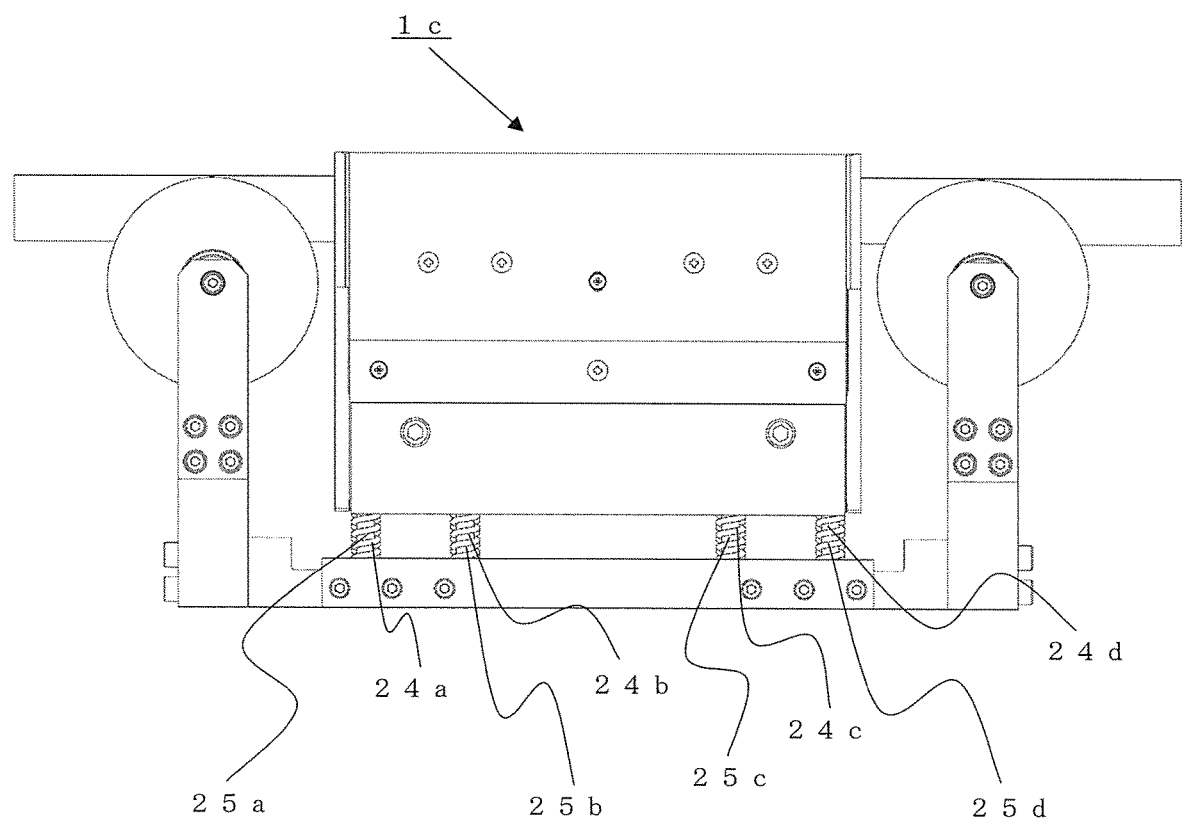
FIG. 10 is a side view of a wire rope flaw detector according to a third embodiment of the present invention.
Figure 11:
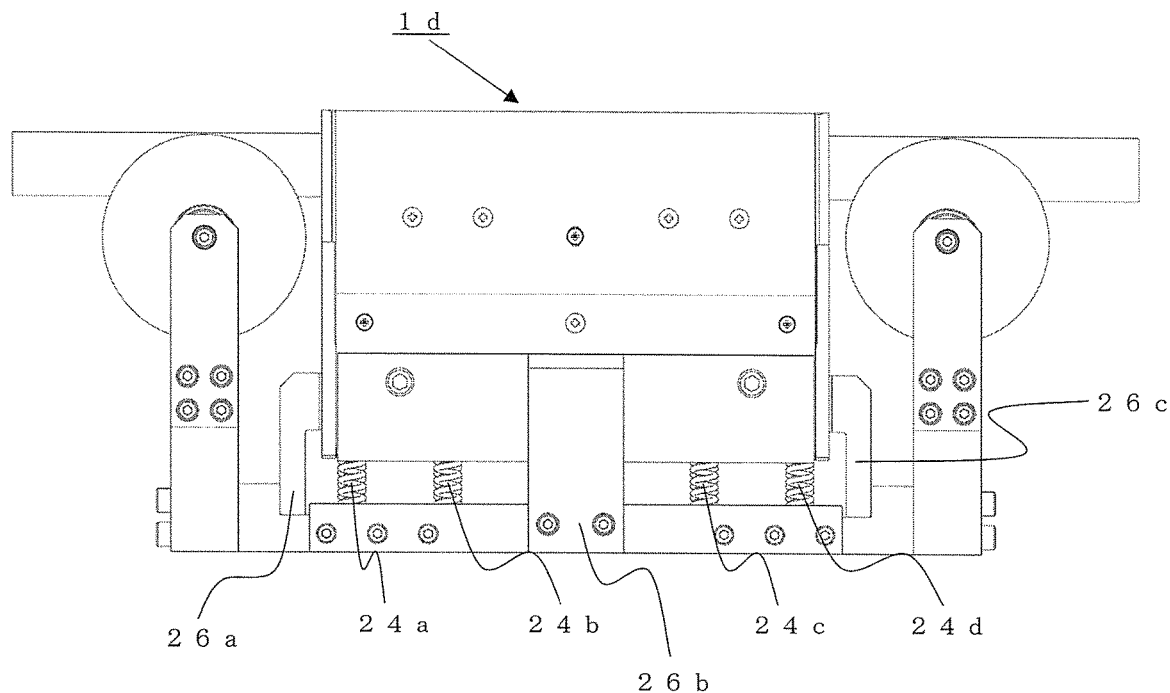
FIG. 11 is a side view of a wire rope flaw detector according to a fourth embodiment of the present invention.
Figure 12:
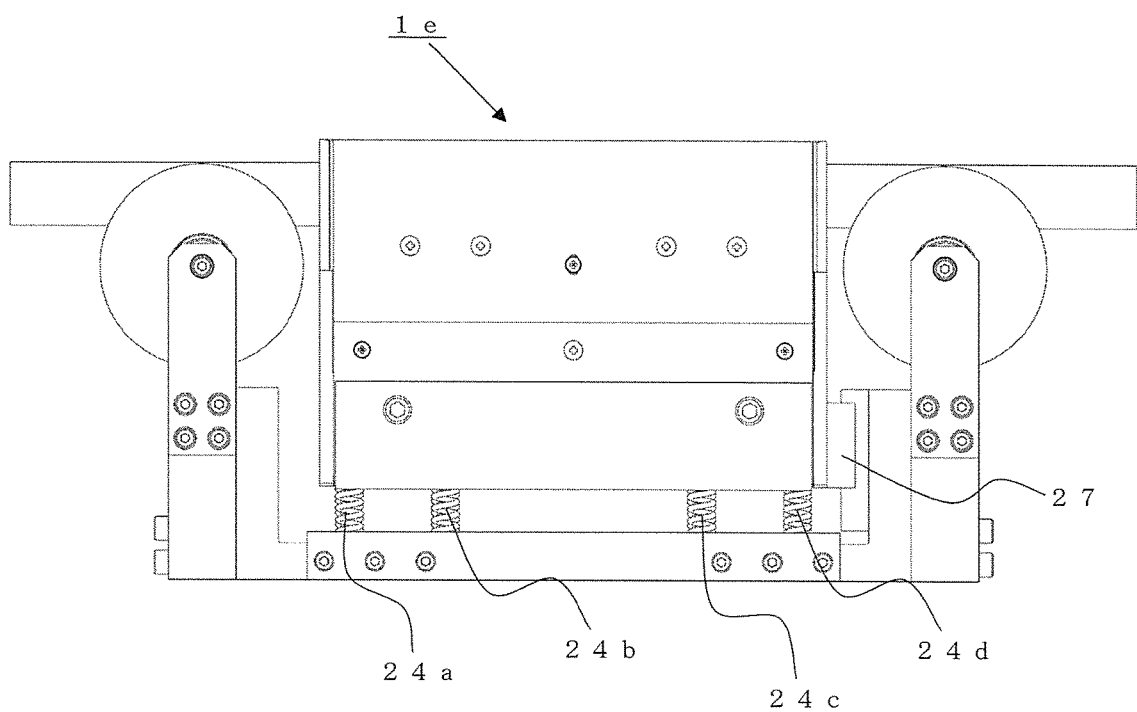
FIG. 12 is a side view of a wire rope flaw detector according to a fifth embodiment of the present invention.

FIG. 10 to FIG. 12 each are side views for illustrating wire rope flaw detectors 1c to 1e according to a third embodiment to a fifth embodiment. Through provision of the buffer members 5a and 5b, such a fact that vibrations generated at contact portions between the wire rope 7a and the guide rollers 17a and 17b is not transmitted to the probe 2 is described above. However, in order to make the change in gap between the wire rope 7a and the detection coils 9 more stable, the vibration in the z direction may be suppressed.

However, in the buffer members described in the first embodiment and the second embodiment, the thermosetting resin or the thermoplastic resin, and the spring may be bent, by the vibration or a self-weight of the probe 2, in the x direction or the y direction, and hence the probe 2 may vibrate in the x direction or the y direction. As a result, depending upon the conditions of the vibration, the change in the gap between the wire rope 7a and the detection coils 9 is liable to be promoted.

To prevent this change in gap, any guide may be provided so that the thermosetting resin or the thermoplastic resin, or the spring is prevented from bending in the x direction or the y direction. For example, there may be given a case, as illustrate in the third embodiment illustrated in FIG. 10, a case in which guide shafts 25a, 25b, 25c, and 25d each are provided inside a center thereof, a case, as illustrated in the fourth embodiment illustrated in FIG. 11, in which guide walls 26a, 26b, and 26c are provided, and further a case, as illustrated in the fifth embodiment illustrated in FIG. 12, in which a linear guide 27 is provided between the probe 2 and the position regulation mechanisms 4a and 4b.

It should be noted that, in FIG. 11, the guide walls 26a, 26b, and 26c and the probe are only brought into contact and are not connected with each other.

Further, all the buffer members illustrated in FIG. 10 to FIG. 12 are constructed of the springs, and are free from a problem even in a case of being constructed by the thermosetting resin or the thermoplastic resin.

With those constructions, the buffer members are free from promoting the change in gap between the wire rope and the detection coil due to the bending of the buffer members in the x direction or the y direction, and hence the gentle change in gap may be achieved to enhance the detection precision of the flaw portion of the wire rope.

Sixth Embodiment

Figure 13:
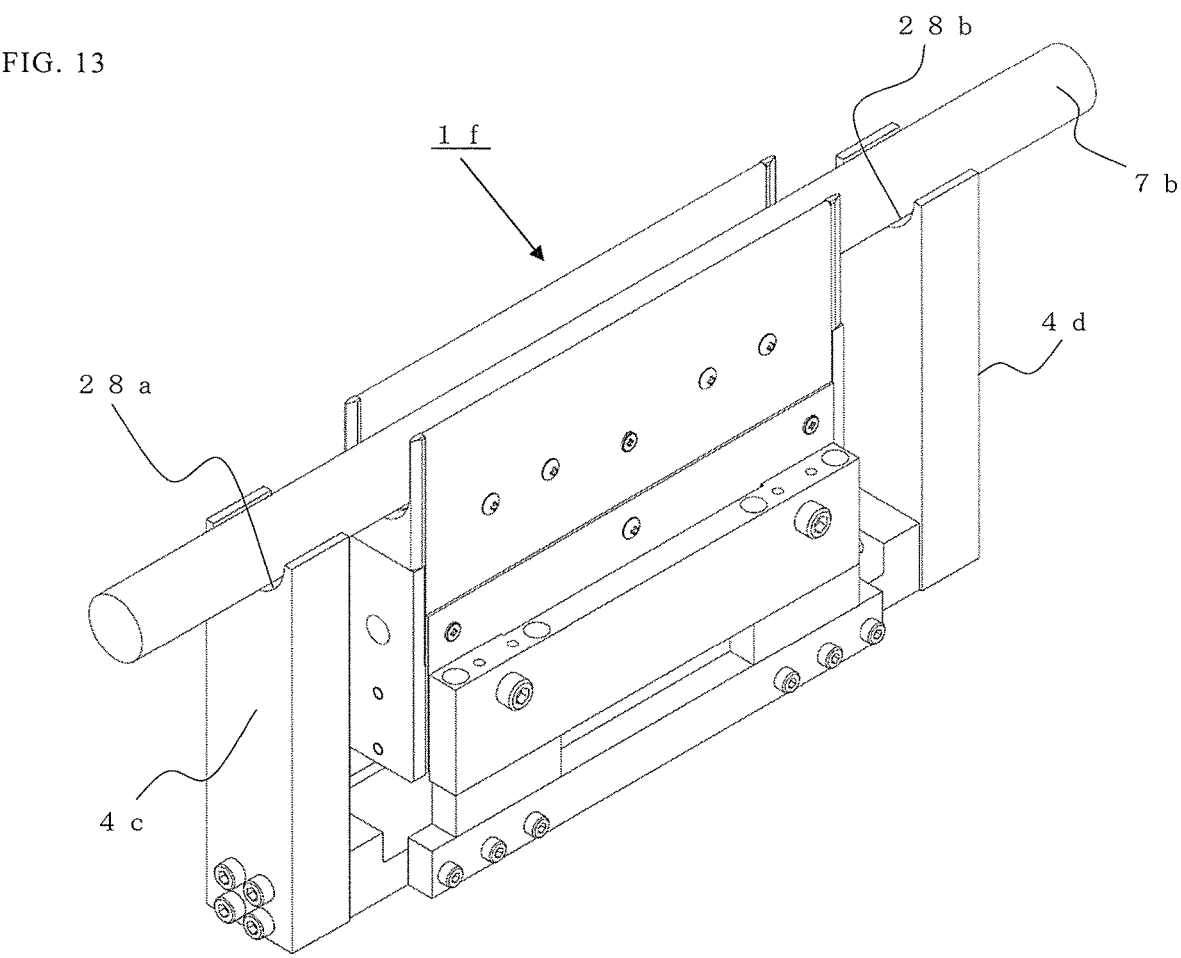
FIG. 13 is a side view of a wire rope flaw detector according to a sixth embodiment of the present invention.

FIG. 13 is an illustration of a wire rope flaw detector 1f according to a sixth embodiment of the present invention. In a case in which a wire rope 7b is coated with a resin, and a case in which a sliding resistance between the wire rope 7b and a metal material is small, or is capable of ignoring its affect, the guide rollers employed in the first embodiment to the fifth embodiment are not required to the position regulation mechanisms 4c and 4d, and as illustrated in FIG. 13, substantially U-shaped guide grooves 28a and 28b may be provided to the ends of the position regulation mechanisms 4c and 4d, respectively, serving as the support base.

According to those constructions, while enhancing the detection precision of the flaw portion of the wire rope, as described in the first embodiment to the fifth embodiment, the number of parts of the wire rope flaw detector may be reduced, thereby being capable of achieving a cost reduction.

The invention claimed is:
1. A wire rope flaw detector, comprising:
  a probe including: a magnetizer configured to form a main magnetic flux so as to embrace a predetermined segment in an axial direction of a wire rope; and a detection coil, which is disposed within the predetermined segment so as to be magnetically insulated from the magnetizer, and is configured to detect leakage of the magnetic flux generated from the damaged portion of the wire rope;
  a first position regulating mechanism and a second position regulating mechanism disposed on both sides of the probe in the axial direction of the wire rope of the magnetizer, which are configured to regulate a position of the probe in association with a running of the wire rope;
  a connecting member configured to connect between the first position regulating mechanism and the second position regulating mechanism; and
  a buffer member provided between the connecting member and the probe, the connecting member and the probe being connected via the buffer member, wherein the buffer member is made of a material that, during running of the wire rope, a vibration frequency of vibration generated by the probe becomes lower than the vibration frequency of vibration generated by each of the first position regulation mechanism and the second position regulation mechanism, and the probe follows the vibration of the wire rope.

2. A wire rope flaw detector according to claim 1, wherein an inherent frequency of vibration of the material of the buffer member is lower than the vibration frequency of vibration generated, during the running of the wire rope, by each of the first position regulation mechanism and the second position regulation mechanism.

3. A wire rope flaw detector according to claim 1, wherein an inherent frequency of the buffer member is larger than the vibration frequency of vibration having a largest amplitude among vibration components of the wire rope.

4. A wire rope flaw detector according to claim 1, wherein the buffer member is made of one of a thermoplastic resin and a thermosetting resin.

5. A wire rope flaw detector according to claim 4, wherein one of the thermoplastic resin and the thermosetting resin is an urethane resin.

6. A wire rope flaw detector according to claim 1, wherein the buffer member comprises a spring satisfying the condition.

7. A wire rope flaw detector according to claim 6, wherein the spring includes inside a center thereof a guide shaft configured to move the probe in a predetermined direction only with respect to the connecting member.

8. A wire rope flaw detector according to claim 1, further comprising guide wall portions configured to guide the probe such that the probe and the connecting member are connected under a contact state, and the probe are moved in a predetermined direction only.

9. A wire rope flaw detector according to claim 1, further comprising a linear guide, which is provided between at least one of the first position regulation mechanism or the second position regulation mechanism and the probe, and is configured to move the probe in a predetermined direction only.

10. A wire rope flaw detector according to claim 1, wherein the first position regulation mechanism and the second position regulation mechanism each comprise a rotatable guide roller and a support base configured to support the guide rollers.

11. A wire rope flaw detector according to claim 1, wherein, when a sliding resistance between each of the first position regulation mechanism and the second position regulation mechanism and the wire rope is small, the first position regulation mechanism and the second position regulation mechanism each comprise a wire rope support base including a substantially U-shaped guide groove, which is brought into direct contact with the wire rope.

12. A wire rope flaw detector according to claim 1, wherein contact portions between each of the first position regulation mechanism and the second position regulation mechanism and the wire rope are arranged to be spaced from a lowest portion of guide groove of the probe so that the wire rope is supported by the first position regulation mechanism and the second position regulation mechanism without contacting the guide groove of the probe.

13. An adjustment jig, which is used for adjustment of a wire rope flaw detector, the wire rope flaw detector, comprising:

a probe including: a magnetizer configured to form a main magnetic flux so as to embrace a predetermined segment in an axial direction of a wire rope; and a detection coil, which is disposed within the predetermined segment so as to be magnetically insulated from the magnetizer, and is configured to detect leakage of the magnetic flux generated from the damaged portion of the wire rope;

a first position regulating mechanism and a second position regulating mechanism disposed on both sides of the probe in the axial direction of the wire rope of the magnetizer, which are configured to regulate a position of the probe in association with a running of the wire rope;

a connecting member configured to connect between the first position regulating mechanism and the second position regulating mechanism; and a buffer member provided between the connecting member and the probe, the connecting member and the probe being connected via the buffer member, wherein the buffer member is made of a material that, during running of the wire rope, a vibration frequency of vibration generated by the probe becomes lower than the vibration frequency of vibration generated by each of the first position regulation mechanism and the second position regulation mechanism;

the adjustment jig comprising:

a guide plate contact portion having a substantially U-shape, which is inserted into a substantially U-shaped portion of guide plates forming the probe; and guide roller contact portions each having a substantially U-shape, which are inserted into substantially U-shaped portions of end portions of the first position regulation mechanism and the second position regulation mechanism, and are shorter in height than the guide plate contact portions so that the wire rope is supported by the first position regulation mechanism and the second position regulation mechanism without contacting with the guide groove of the probe.

14. An adjustment jig according to claim 13, wherein the guide plate contact portion comprises a ferromagnetic material, and is attracted to a permanent magnet provided in the probe at an initial adjustment.

* * * * *